US009758716B2

(12) United States Patent
Roccon

(10) Patent No.: US 9,758,716 B2
(45) Date of Patent: *Sep. 12, 2017

(54) PROCESS FOR TREATING A WASTEWATER STREAM PRODUCED BY HYDROCARBON PRODUCTION OPERATIONS FOR REPURPOSING AS A DISINFECTANT FOR HYDROCARBON PRODUCTION OPERATIONS

(71) Applicant: Raymond J Roccon, Harmony, PA (US)

(72) Inventor: Raymond J Roccon, Harmony, PA (US)

( * ) Notice: Subject to any disclaimer, the term of this patent is extended or adjusted under 35 U.S.C. 154(b) by 236 days.

This patent is subject to a terminal disclaimer.

(21) Appl. No.: 14/812,172

(22) Filed: Jul. 29, 2015

(65) Prior Publication Data

US 2016/0017209 A1 Jan. 21, 2016

Related U.S. Application Data

(63) Continuation of application No. 13/934,252, filed on Jul. 3, 2013, now Pat. No. 9,120,966.

(60) Provisional application No. 61/667,601, filed on Jul. 3, 2012.

(51) Int. Cl.
| C09K 8/74 | (2006.01) |
| E21B 43/26 | (2006.01) |
| C09K 8/66 | (2006.01) |
| C09K 8/60 | (2006.01) |
| E21B 21/06 | (2006.01) |
| C02F 1/76 | (2006.01) |
| A01N 59/00 | (2006.01) |
| C02F 1/66 | (2006.01) |

(52) U.S. Cl.
CPC ............... *C09K 8/66* (2013.01); *A01N 59/00* (2013.01); *C02F 1/76* (2013.01); *C09K 8/605* (2013.01); *E21B 21/068* (2013.01); *C02F 1/66* (2013.01); *C02F 2303/04* (2013.01)

(58) Field of Classification Search
CPC .................................. C09K 8/605; C09K 8/66

USPC ........................................................ 507/269
See application file for complete search history.

(56) References Cited

U.S. PATENT DOCUMENTS

| 5,015,643 | A | 5/1991 | Jones et al. |
| 5,464,636 | A | 11/1995 | Hight et al. |
| 5,476,670 | A | 12/1995 | Hight et al. |
| 5,527,547 | A | 6/1996 | Hight et al. |
| 5,543,388 | A | 8/1996 | Williams et al. |
| 5,662,940 | A | 9/1997 | Hight et al. |
| 6,927,237 | B2 | 8/2005 | Hei et al. |
| 7,531,080 | B2 | 5/2009 | Carson et al. |
| 9,120,966 | B2 | 9/2015 | Roccon |
| 2006/0182816 | A1 | 8/2006 | Shane et al. |
| 2011/0287984 | A1 | 11/2011 | Mirakyan et al. |
| 2015/0329387 | A1* | 11/2015 | Sumrall ............... C02F 1/70 210/754 |

OTHER PUBLICATIONS

Shawn M. Rimassa, Paul Howard, Bruce Mackay, Kristel Blow, Noel Coffman, SPE, Schlumberger, Case Study: Evaluation of an Oxidative Biocide During and After a Hydraulic Fracturing Job in the Marcellus Shale, Apr. 2011, Society of Petroleum Engineers, Prepared for Presentation at the SPE International Symposium on Oilfield Chemistry held in The Woodlands, Texas.

* cited by examiner

*Primary Examiner* — Aiqun Li
(74) *Attorney, Agent, or Firm* — Blynn L. Shideler; Krisanne Shideler; BLK Law Group

(57) ABSTRACT

A method of treating wastewater resulting from hydrocarbon production operations is provided, for repurposing as a disinfectant. The method includes a) providing wastewater resulting from hydrocarbon production operations containing greater than 3 ppm bromide ion; and b) adding a sufficient amount of an oxidizing agent to convert the bromide ion to hypobromous acid used in the formation of a disinfectant solution. At least one of chloramine, bromamine, and hypobromous acid is present in the disinfectant solution to provide disinfecting properties. A source of ammonia may also be added to the wastewater, and the disinfectant solution may be blended with other water to provide blended water for use as a fracturing fluid.

20 Claims, No Drawings

PROCESS FOR TREATING A WASTEWATER STREAM PRODUCED BY HYDROCARBON PRODUCTION OPERATIONS FOR REPURPOSING AS A DISINFECTANT FOR HYDROCARBON PRODUCTION OPERATIONS

RELATED APPLICATIONS

This application a continuation-in-part of U.S. patent application Ser. No. 13/934,252 filed Jul. 3, 2013, entitled "Process for Disinfecting and Stabilizing Production Water using In-situ Hypobromous Acid Generation", which published Jan. 9, 2014 as Publication 2014-0011716, which publication is incorporated herein by reference, and which application issued as U.S. Pat. No. 9,120,966, which publication is incorporated herein by reference.

U.S. patent application Ser. No. 13/934,252 claims the benefit of U.S. Provisional Patent Application Ser. No. 61/667,601, filed Jul. 3, 2012, and entitled "Process for Disinfecting and Stabilizing Production Water using In-situ Hypobromous Acid Generation," which is herein incorporated by reference.

BACKGROUND INFORMATION

1. Field of the Invention

The present invention relates to methods of treating a wastewater stream produced from hydrocarbon production operations for repurposing as a disinfectant used in hydrocarbon production operations.

2. Background Information

Aqueous treatment fluids may be used in a variety of subterranean treatments. Such treatments include, but are not limited to, drilling operations, stimulation operations, and completion operations. As used herein, the term "treatment," or "treating," refers to any subterranean operation that uses a fluid in conjunction with a desired function and/or for a desired purpose. The term "treatment," or "treating," does not imply any particular action by the fluid.

One example of a treatment fluid are viscous gelled fracturing fluids commonly utilized in the hydraulic fracturing of subterranean zones penetrated by well bores to increase the production of hydrocarbons from the subterranean zones. That is, a viscous fracturing fluid is pumped through the well bore into a subterranean zone to be stimulated at a rate and pressure such that fractures are formed and extended into the subterranean zone. The fracturing fluid also carries particulate proppant material, e.g., graded sand, into the formed fractures. The proppant material is suspended in the viscous fracturing fluid so that the proppant material is deposited in the fractures when the viscous fracturing fluid is broken and recovered. The proppant material functions to prevent the fractures from closing whereby conductive channels are formed through which produced fluids can flow to the well bore.

An example of a stimulation operation utilizing an aqueous treatment fluid is hydraulic fracturing. In some instances, a fracturing treatment involves pumping a proppant-free, aqueous treatment fluid (known as a pad fluid) into a subterranean formation faster than the fluid can escape into the formation so that the pressure in the formation rises and the formation breaks, creating or enhancing one or more fractures. Enhancing a fracture includes enlarging a pre-existing fracture in the formation. Once the fracture is formed or enhanced, proppant particulates are generally placed into the fracture to form a proppant pack that may prevent the fracture from closing when the hydraulic pressure is released, forming conductive channels through which fluids may flow to the well bore.

In many cases, soluble salts from down-hole formations dissolve into the fluids used in the hydraulic fracturing process and are returned to the surface in the form of produced and flowback waters. These waters are considered wastewaters that are typically disposed of through chemical or thermal treatment or injection into disposal wells. However, due to government regulation and the volume of wastewater produced, it is becoming more difficult to properly dispose of wastewater resulting from hydrocarbon production operations.

There is a need in the art to provide alternative uses for the wastewater resulting from hydrocarbon production operations in order to avoid the need to dispose of it.

SUMMARY OF THE INVENTION

In order to overcome these deficiencies in the prior art, the present invention provides a method of reusing wastewater resulting from hydrocarbon production operations as a disinfectant. The method includes a) providing wastewater resulting from hydrocarbon production operations containing greater than 3 ppm bromide ion; b) if scale control is desired, adjusting the pH of the wastewater to less than 8.5; and c) adding a sufficient amount of an oxidizing agent to convert the bromide ion to hypobromous acid to provide a disinfectant solution.

The present invention is also directed to a method of reusing wastewater resulting from hydrocarbon production operations as a disinfectant that includes a) providing wastewater resulting from hydrocarbon production operations containing greater than 3 ppm bromide ion; b) if scale control is desired, adjusting the pH of the wastewater to less than 8.5; c) adding a sufficient amount of an oxidizing agent to convert the bromide ion to hypobromous acid to provide a disinfectant solution; d) blending the disinfectant solution with other water to provide a fracturing fluid comprising at least 5 ppm bromide; e) if scale control is desired, adjusting the pH of the blended water to a range that prevents the formation of scale-forming salts; f) maintaining a free bromine level is at least 0.1 ppm.

The present invention further provides a method of treating a wastewater stream produced from hydrocarbon production operations for repurposing as a disinfectant used in hydrocarbon production operations comprising: a) providing wastewater resulting from hydrocarbon production operations containing greater than 3 ppm bromide ion; b) adding a sufficient amount of an oxidizing agent and a source of ammonia, if sufficient ammonia is not already present in the wastewater, to yield at least one of a chloramine and a bromamine in amounts sufficient to provide a disinfectant solution for use in hydrocarbon production operations.

Additionally, a method of reusing wastewater resulting from hydrocarbon production operations as a disinfectant is provided, comprising: a) providing wastewater resulting from hydrocarbon production operations containing greater than 3 ppm bromide ion; b) adding a sufficient amount of an oxidizing agent to convert the bromide ion to hypobromous acid used in the formation of a disinfectant solution, wherein at least one of chloramine, bromamine, and hypobromous acid is present in the disinfectant solution to provide disinfecting properties; and c) blending the disinfectant solution with other water to provide blended water in a fracturing fluid.

The features that characterize the present invention are pointed out with particularity in the claims which are part of this disclosure. These and other features of the invention, its operating advantages and the specific objects obtained by its use will be more fully understood from the following detailed description.

DESCRIPTION OF THE PREFERRED EMBODIMENTS

Other than in the operating examples, or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

Further within the meaning of the present application, "chloramines" are derivatives of ammonia by substitution of 1 or 2, or theoretically 3, hydrogen atoms in the ammonia molecule with chlorine atoms and "bromamines" are derivatives of ammonia by substitution of 1 or 2, or theoretically 3, hydrogen atoms in the ammonia molecule with bromine atoms. Typically, these haloamines are mono- or di-substituted.

The present invention provides alternative uses for the wastewater resulting from hydrocarbon production operations in order to avoid the need to dispose of such wastewater; and more directly to methods of disinfecting and stabilizing water produced from hydrocarbon production operations. Thus, in many respects, the invention provides methods of reusing salt-laden wastewater from hydrocarbon production operations as a halogen source for disinfecting fluids used in subsequent hydraulic fracturing operations, by in-situ halogen generation from the bromide salt as well as methods of maximizing the conversion of bromide salt into disinfectant by adjusting the pH downward to a pH that has been calculated to make the total fluid non-scaling.

In embodiments of the invention, the wastewater resulting from hydrocarbon production operations an contain various heavy metals, polymers and other additives removed from down hole formations or otherwise used in hydrocarbon production operations. In this embodiment other methods known in the art can be used to remove certain materials from the wastewater.

In the present method, wastewater resulting from hydrocarbon production operations is reused as a disinfectant. The method broadly includes the steps of providing wastewater resulting from hydrocarbon production operations containing greater than 3 ppm bromide ion; if scale control is desired, adjusting the pH of the wastewater to less than 8.5; and adding a sufficient amount of an oxidizing agent to convert the bromide ion to hypobromous acid to provide a disinfectant solution.

Typically, the wastewater resulting from hydrocarbon production operations contain moderate to high levels of bromide ion. The amount of bromide ion in the wastewater that can be used in the invention can vary, but is typically at least 3 ppm. In embodiments of the invention, the amount of bromide ion in the wastewater can be at least 5 ppm, in some cases at least 6 ppm, in some instances at least 8 ppm and in other instances at least 10 ppm and can be up to 10,000 ppm, in some cases up to 7,500 ppm, in other cases up to 5,000 ppm, in some instances up to 2,500 ppm and in other instances up to 1,000 ppm. The amount of bromide ion in the wastewater used in the invention can be any value or range between any of the values recited above. The particular amount of bromide ion that can be present in the wastewater will depend on the other constituents in the wastewater and processing parameters described herein.

In the present invention, bromide ion is oxidized to form hypobromous acid, which is a strong disinfectant. The oxidation of bromide ion can be accomplished using any suitable oxidizing agent. Suitable oxidizing agents include, but are not limited to one or more of ozone, chlorine gas, hypochlorites such as sodium hypochlorite and calcium hypochorite, dichloro isocyanuranate, and trichloroisocyanuric acid.

In embodiments of the invention, the oxidizing agent can increase the pH of the wastewater, which can cause the conversion of bromide to hypobromous acid to be less efficient. Thus, in these embodiments of the invention, a suitable acid is used to lower the pH of the wastewater to promote the conversion of bromide to hypobromous acid. Any suitable acid can be used to lower the pH. In many cases it is desirable to use an inorganic acid to lower the pH of the wastewater. In particular embodiments of the invention, hydrochloric acid is used to lower the pH of the wastewater.

In embodiments of the invention, if scale control is desired the pH of the wastewater is adjusted to 8.5 or less, in some cases 8.0 or less, in other cases 7.5 or less, in some instances 7 or less, in other instances 6.5 or less and in some situations 6 or less. The pH is adjusted to a level that maximizes the conversion of bromide to hypobromous acid and minimizes the formation of scale forming salts.

In embodiments of the invention, the oxidizing agent and acid for pH control are independently or simultaneously added to the wastewater or the wastewater/makeup water blend which can constitute a fracturing fluid.

Alternatively, in situations where pH stabilization may not be required or desired, adequate disinfectant properties of the water may still be accomplished by increasing the amount of oxidizing agent added, to compensate for any hypobromous acid not formed due to higher system pH.

As used herein the term "scale forming salts" refers to salts of divalent or multivalent metals, including but not limited to calcium, magnesium and iron, that tend to precipitate onto surfaces when present at elevated concentrations in the wastewater and at pH levels that promote precipitation. Scale forming salts include, but are not limited to one or more carbonate, sulfate, phosphate, silicate, oxide and/or hydroxide salts of calcium, magnesium, iron, barium, strontium, and/or radium.

Subsequently, wastewater resulting from hydrocarbon production operations can be analyzed and then blended with other water sources to form a blended water, which can be fracturing fluid. The blended water is typically blended to have a bromide ion concentration of at least 1 ppm, such as at least 3 ppm. In embodiments of the invention, the amount of bromide ion in the blended water used in the invention can vary, but can be at least 5 ppm, often at least 6 ppm, in some cases at least 7 ppm, in some instances at least 9 ppm and in other instances at least 10 ppm and can be up to 10,000 ppm, in some cases up to 7,500 ppm, in other cases up to 5,000 ppm, in some instances up to 2,500 ppm and in other instances up to 1,000 ppm. The amount of bromide ion in the blended water of the invention can be any value or range between any of the values recited above.

In embodiments of the invention, analysis of the blended water can predict the correct pH to minimize the tendency of scale forming salts to precipitate from the blended water.

In embodiments of the invention, an oxidizing agent and, if scale control is desired, a pH adjusting acid as disclosed above can be added separately to the blended water. Alternatively, an oxidizing agent and, if scale control is desired, a pH adjusting acid can be added simultaneously using in process control equipment known in the art. As disclosed above, if desired both the oxidizing agent and pH are adjusted to maximize the formation of hypobromous acid and to minimize the formation of scale forming salts.

In embodiments of the invention, testing and control of pH and oxidizing agent can be automated. Alternatively, commercially available test kits can be used to allow an operator use breakpoint bromination techniques. In other words, testing can be conducted for both free and total chlorine/bromine. Once all of the halogen demand of the blended water is satisfied, free residual chlorine/bromide can be detected in the blend water.

In embodiments of the invention, the blend water will contain at least 0.1 ppm, in some cases at least 0.2 ppm, in other cases at least 0.5 ppm, in other cases at least 1 ppm, in some instances at least 2 ppm, in other instances at least 5, in some situations at least 7.5 ppm, and in other situations at least 10 ppm free residual bromine as bromide ion. The amount of free residual bromine will be an amount sufficient to disinfect the particular blended water.

In embodiments of the invention, the present methods can be automated using real-time probes that are in communication with monitoring and control equipment known in the art to monitor and control the feed rates of pH adjusting acid and oxidizing agent to automatically adjust to changes in the composition of blend water.

The above described process or method is one of treating a wastewater stream produced from hydrocarbon production operations for repurposing as a disinfectant used in hydrocarbon production operations. The hypobromous acid kills bacteria but may also form a disinfection by-product known as THM's (trihalomethanes). The THMs produced have been associated through epidemiological studies with some adverse health effects. Many governments set limits on the amount permissible in drinking water. For example, in the United States, the EPA limits the total concentration of the four chief constituents (chloroform, bromoform, bromodichloromethane, and dibromochloromethane), referred to as total trihalomethanes (TTHM), to 80 parts per billion in treated water.

While oilfield operations are not subject to potable water restrictions, it may be of benefit to modify the present process or method of treating a wastewater stream produced from hydrocarbon production operations for repurposing as a disinfectant used in hydrocarbon production operations that will not form THM's. Specifically, a source of ammonia, if ammonia is not already present in sufficient quantities in the wastewater stream, may be added to water systems where chlorine and bromide ions are present, to immediately combine with the chlorine or hypobromous acid to form chloramine or bromamine. Both chloramine and bromamine reduce the potential of THM formation significantly, thereby allowing disinfection with chlorine/bromine and still meeting the 80 ppb THM limit.

Suitable sources of ammonia include anhydrous ammonia itself ($NH_3$), ammonium hydroxide, and ammonium salts that may generate ammonia in solution such as ammonium sulfates, ammonium nitrates, ammonium halides such as ammonium chloride, and the like.

In this aspect of the present invention, a method of treating a wastewater stream produced from hydrocarbon production operations for repurposing as a disinfectant used in hydrocarbon production operations is provided, comprising: a) providing wastewater resulting from hydrocarbon production operations containing greater than 3 ppm bromide ion; and b) adding a sufficient amount of an oxidizing agent and a source of ammonia, if ammonia is not already present in sufficient amounts in the wastewater stream, to yield at least one of a chloramine and a bromamine in amounts sufficient to provide a disinfectant solution for use in hydrocarbon production operations. As known to those in the art, wastewater streams may contain ammonia, and thus the wastewater itself may form a source of ammonia where present in sufficient amounts for the chemistry set forth herein.

Note that the disinfectant solution may be blended with other water to provide a fracturing fluid comprising at least 1 ppm bromide, such as at least 2 ppm bromide. When blended, the pH of the fracturing fluid is typically in a range that minimizes the formation of scale-forming salts.

In one embodiment, a source of ammonia would be added subsequent to the oxidizing agent addition. Note that the oxidizing agent may be any of those disclosed above. In this way, addition of oxidizing agent such as sodium hypochlorite to the wastewater containing bromide ion leads to the formation of hypobromous acid, as discussed above. The subsequent addition of a source of ammonia combines with the hypobromous acid to form bromamines (mono- and/or dibromoamine), excellent biocides which are only slightly less effective than hypobromous acid. The formed bromamine will not form THM's.

The following reactions would be expected to occur:

$$HBrO+NH_3 \leftrightarrow NH_2Br+H_2O$$

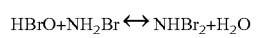

$$HBrO+NH_2Br \leftrightarrow NHBr_2+H_2O$$

In an alternative embodiment, a source of ammonia would be added to the wastewater stream produced from hydrocarbon production operations upstream of (prior to), or alternatively simultaneously with, the oxidizing agent addition. Adding a source of ammonia first in the presence of bromide ions will yield bromochloramine. Specifically considering sodium hypochlorite as the oxidizing agent, this process will form chloramine in the presence of bromide ion. Sodium hypochlorite's affinity for ammonia will supersede its reaction with bromide ion, so addition of sodium hypochlorite to a wastewater stream containing both bromide ion and ammonia will produce chloramine in the presence of bromide ion. Based on the efficacy of the ammonium bromide product, it is believed that this modified method is eventually forming bromamine during the reaction.

The following reactions are expected to occur:

$$NH_2Cl+H+\rightleftharpoons NH_3Cl^+$$

$$NH_3Cl^++Br-\rightarrow NH_3Br^++Cl-$$

$$NH_3Br^++NH_2Cl\rightarrow NHClBr+NH_4^+$$

NHClBr may react further with $Br^-$ to form dibromamine:

$$NHClBr+Br-\rightleftharpoons NHBr_2+Cl-$$

A possible formation of $NH_2Br$ is also by an $SN_2$ mechanism:

$$NH_2Cl+Br-\rightarrow NH_2Br+Cl-$$

The hydrolysis of monochloramine, though slow, can also result in monobromoamine:

$$NH_2Cl+H_2O\rightleftharpoons HClO+NH_3$$

$$HClO+Br-\rightarrow HBrO+Cl-$$

$$HBrO+NH_3\rightarrow NH_2Br+H_2O$$

In a separate embodiment of the present invention, a method of reusing wastewater resulting from hydrocarbon production operations as a disinfectant is provided, comprising: a) providing wastewater resulting from hydrocarbon production operations containing greater than 3 ppm bromide ion; b) adding a sufficient amount of an oxidizing agent, such as any of those disclosed above, to convert the bromide ion to hypobromous acid used in the formation of a disinfectant solution, wherein at least one of chloramine, bromamine, and hypobromous acid is present in the disinfectant solution to provide disinfecting properties; and c) blending the disinfectant solution with other water to provide blended water in a fracturing fluid. This process may further comprise the step of adding a source of ammonia subsequent to the addition of the oxidizing agent, typically before blending with other water. Bromamine is yielded upon addition of the ammonia source to provide the disinfectant solution for use in hydrocarbon production operations.

The methods according to the invention provide numerous advantages. As a non-limiting example, the blend water costs less than a freshly formulated fracturing fluid because it utilizes the formed hypobromous acid instead of expensive specialty biocides. Further, the readily available monitoring and control techniques described above provide for improved feed control, lower volumes of chemicals, and less manpower to obtain desired results and lower overall processing costs. The fact that no additional bromide is added to the blend water in the disinfection process provides a particular cost savings. Additionally, rather than using separate monitoring and control operations, disinfection and scale control are combined in one step.

EXAMPLES

To more clearly illustrate the present invention, the following example is presented below. This example is intended to be illustrative and no limitations to the present invention should be drawn or inferred from the examples presented herein.

Example 1

Marcellus production wastewater is obtained from a hydraulic fracturing operation containing 300 mg/l barium, 110 mg/l bromide, 890 mg/l calcium, 75 mg/l lithium, 456 mg/l magnesium, 40,000 mg/l sodium, 480 mg/l bicarbonate 65,000 mg/l chloride and 650 mg/l strontium. This production water is blended 20:80 with fresh water to provide blended water containing 22 mg/l bromide ion. The blended water is then evaluated using an index that predicts scale formation potential. If the blended water exhibits calcite scaling tendencies, hydrochloric acid is added to the wastewater to adjust the pH to the point where the predictive index shows the pH adjusted blended water to be non-scaling or slightly scale dissolving with regard to calcite. Sodium hypochlorite (oxidizing agent) is then added to the pH adjusted blended water, converting the bromide ion to hypobromous acid at levels adequate to disinfect the full volume of blended water. Because of the dissociation relationship of bromine to hypobromous acid and hypobromite ion, lowering of the fluid pH to prevent calcite scaling has the additional benefit of favoring the formation of hypobromous acid as compared to hypobromite ion, where hypobromous acid is acknowledged as a superior biological disinfectant. This blended water is used as the base fluid for performing a subsequent hydraulic fracturing operation. Utilization of bromide present in produced water to form the fracturing fluid disinfectant while adjusting pH to minimize calcite scale significantly reduces the cost of fracturing fluid disinfection and scale prevention, does not add additional bromide ion to the water table and prevents biological inoculation of the well.

While the invention has been shown in several particular embodiments it should be clear that various modifications may be made to the present invention without departing from the spirit and scope thereof. The scope of the present invention is defined by the appended claims and equivalents thereto.

What is claimed is:

1. A method of treating a wastewater stream produced from hydrocarbon production operations for repurposing as a disinfectant used in hydrocarbon production operations comprising:
    a) providing wastewater resulting from hydrocarbon production operations in which the bromide ion concentration is known to be greater than 3 ppm bromide ion; and
    b) adding a sufficient amount of an oxidizing agent to the wastewater and providing a source of ammonia to yield at least one of a chloramine and a bromamine in amounts sufficient to provide a disinfectant solution for use in hydrocarbon production operations.

2. The method according to claim 1, wherein the oxidizing agent is one or more selected from the group consisting of ozone, chlorine gas, sodium hypochlorite, dichloro isocyanuranate, and trichloroisocyanuric acid.

3. The method according to claim 2, wherein at least part of the source of ammonia is added to the wastewater and wherein the oxidizing agent is added prior to the addition of ammonia.

4. The method according to claim 3, wherein the oxidizing agent is sodium hypochlorite.

5. The method according to claim 4, wherein at least bromamine is yielded in step b) to provide the disinfectant solution for use in hydrocarbon production operations.

6. The method according to claim 5, wherein the disinfectant solution is blended with other water to provide a fracturing fluid comprising at least 1 ppm bromide.

7. The method according to claim 6, wherein the pH of the fracturing fluid is in a range that minimizes the formation of scale-forming salts.

8. The method according to claim 5, wherein the disinfectant solution is blended with other water to provide a fracturing fluid comprising at least 2 ppm bromide.

9. The method according to claim 2, wherein the ammonia concentration is greater than 3 ppm prior to the addition of the oxidizing agent.

10. The method according to claim 9, wherein the oxidizing agent is sodium hypochlorite.

11. The method according to claim 10, at least chloramine is yielded in step b) to provide the disinfectant solution for use in hydrocarbon production operations.

12. The method according to claim 11, wherein the disinfectant solution is blended with other water to provide a fracturing fluid comprising at least 1 ppm bromide.

13. The method according to claim 12, wherein the pH of the fracturing fluid is in a range that minimizes the formation of scale-forming salts.

14. A method of reusing wastewater resulting from hydrocarbon production operations as a disinfectant comprising:
 a) providing wastewater resulting from hydrocarbon production operations in which the bromide ion concentration is known to be greater than 3 ppm bromide ion;
 b) adding a sufficient amount of an oxidizing agent to convert the bromide ion to hypobromous acid used in the formation of a disinfectant solution, wherein at least one of chloramine, bromamine, and hypobromous acid is present in the disinfectant solution to provide disinfecting properties; and
 c) blending the disinfectant solution with other water to provide blended water for use as a fracturing fluid.

15. The method according to claim 14
 a) further comprising the step of adding a source of ammonia subsequent to the addition of the oxidizing agent.

16. The method according to claim 15, wherein the oxidizing agent is sodium hypochlorite.

17. The method according to claim 16, wherein bromamine is yielded upon addition of the source of ammonia to provide the disinfectant solution for use in hydrocarbon production operations.

18. The method according to claim 17, wherein the disinfectant solution is blended with other water to provide a fracturing fluid comprising at least 1 ppm bromide.

19. The method according to claim 14, wherein hypobromous acid is yielded in step b) to provide the disinfectant solution for use in hydrocarbon production operations.

20. The method according to claim 19, wherein the disinfectant solution is blended with other water to provide a fracturing fluid comprising at least 2 ppm bromide.

* * * * *